(12) United States Patent
Woodard et al.

(10) Patent No.: US 11,006,967 B2
(45) Date of Patent: May 18, 2021

(54) CARTILAGE REMOVAL TOOL AND METHOD

(71) Applicant: Wright Medical Technology, Inc., Memphis, TN (US)

(72) Inventors: Joseph Ryan Woodard, Memphis, TN (US); Paul Luttrell, Germantown, TN (US); Brian Robert Thoren, Memphis, TN (US); Erin Muller, Lakeland, TN (US); Terrance W. Strohkirch, Memphis, TN (US); Gary W. Lowery, Eads, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 0 days.

(21) Appl. No.: 16/059,190

(22) Filed: Aug. 9, 2018

(65) Prior Publication Data
US 2020/0046377 A1 Feb. 13, 2020

(51) Int. Cl.
*A61B 17/16* (2006.01)
*A61B 17/17* (2006.01)

(52) U.S. Cl.
CPC ...... *A61B 17/1659* (2013.01); *A61B 17/1604* (2013.01); *A61B 17/1682* (2013.01); *A61B 17/164* (2013.01); *A61B 17/1735* (2013.01)

(58) Field of Classification Search
CPC ... A61B 17/144; A61B 17/16; A61B 17/1604; A61B 17/1641; A61B 17/1659; A61B 17/1682; A61B 17/1686; A61B 17/1735; A61B 2017/320004; A61B 2017/320008; A61B 2017/320074
See application file for complete search history.

(56) References Cited

U.S. PATENT DOCUMENTS

| | | | | |
|---|---|---|---|---|
| 2,295,317 A | * | 9/1942 | Young | A43D 37/005 69/6.5 |
| 4,696,292 A | * | 9/1987 | Heiple | A61B 17/164 606/79 |
| 5,080,588 A | * | 1/1992 | O'Brien | A61C 3/02 433/165 |
| 6,048,345 A | | 4/2000 | Berke et al. | |
| 6,083,228 A | | 7/2000 | Michelson | |

(Continued)

FOREIGN PATENT DOCUMENTS

WO 2013109708 A1 7/2013

OTHER PUBLICATIONS http://www.bigceramicstore.com/kemper-8-dual-end-ribbon-tool-8r1-20346.html, "Kemper 8" Ribbon Tool Sculpting Set," May 14, 2018.

(Continued)

*Primary Examiner* — Larry E Waggle, Jr.
(74) *Attorney, Agent, or Firm* — Duane Morris LLP

(57) ABSTRACT

An instrument for use in cartilage removal comprises an elongate body having a first end and a longitudinal axis having a longitudinal direction. A cartilage removal portion is coupled to the elongate body at the first end. The cartilage removal portion includes a plurality of serrated blades substantially perpendicular to the longitudinal axis and adapted for removing material while moving in the longitudinal direction. Each serrated blade has a centroid located along the longitudinal axis.

7 Claims, 9 Drawing Sheets

(56) References Cited

U.S. PATENT DOCUMENTS

| | | | |
|---|---|---|---|
| 8,062,298 B2 * | 11/2011 | Schmitz | A61B 17/00234 |
| | | | 606/79 |
| 8,273,088 B2 | 9/2012 | Zalenski et al. | |
| 8,529,568 B2 | 9/2013 | Bouadi | |
| 8,845,638 B2 * | 9/2014 | Siegal | A61B 17/1671 |
| | | | 606/80 |
| 9,033,986 B2 * | 5/2015 | Nelson | A61B 17/1624 |
| | | | 606/171 |
| 9,232,953 B2 * | 1/2016 | Bono | A61B 17/32002 |
| 9,622,823 B2 | 4/2017 | Bozung et al. | |
| 9,962,170 B2 | 5/2018 | Jansen et al. | |
| 2005/0137600 A1 | 6/2005 | Jacobs et al. | |
| 2007/0233131 A1 | 10/2007 | Song et al. | |
| 2007/0270711 A1 | 11/2007 | Gil et al. | |
| 2011/0071527 A1 | 3/2011 | Nelson et al. | |
| 2013/0211408 A1 * | 8/2013 | Kather | A61B 17/1617 |
| | | | 606/83 |
| 2013/0304070 A1 | 11/2013 | Nelson et al. | |
| 2014/0100574 A1 | 4/2014 | Bono et al. | |
| 2014/0148835 A1 | 5/2014 | Schmitz et al. | |
| 2017/0079735 A1 * | 3/2017 | Baertich | A61B 50/3001 |
| 2018/0078276 A1 | 3/2018 | Chen et al. | |

OTHER PUBLICATIONS

Wright Medical Group N.V., "Ortholoc 3Di, Foot Reconstruction System: Crosscheck Module, Surgical Technique Guide," Aug. 22, 2016.
https://www.alibaba.com/product-detail/Carbide-Rotary-Burrs-RotAry-Burrs-Tungsten_60238689786.html, "Carbide RotAry Burrs/Tungsten Carbid Rotary File," Apr. 16, 2018.
European Search Report issued in connection with European Patent Application No. 18197398.3, dated Oct. 11, 2019, 11 pages.
Office Action issued in connection with corresponding Canadian Patent Application No. 3,017,271, dated Sep. 10, 2019, 5 pages.
First Examination Report issued in connection with corresponding Australian Patent Application No. 2018229467, dated Jul. 26, 2019, 7 pages.
Partial European Search Report issued in connection with European Patent Application No. 18197398.3, dated Jul. 8, 2019, 14 pages.

* cited by examiner

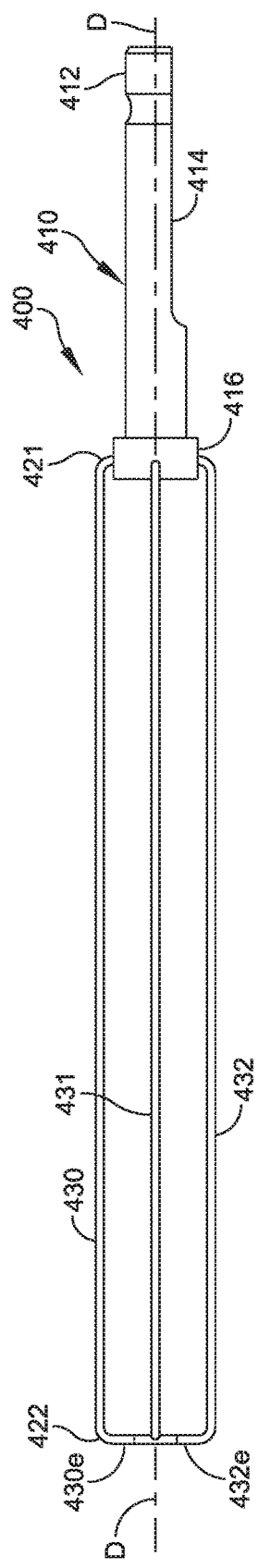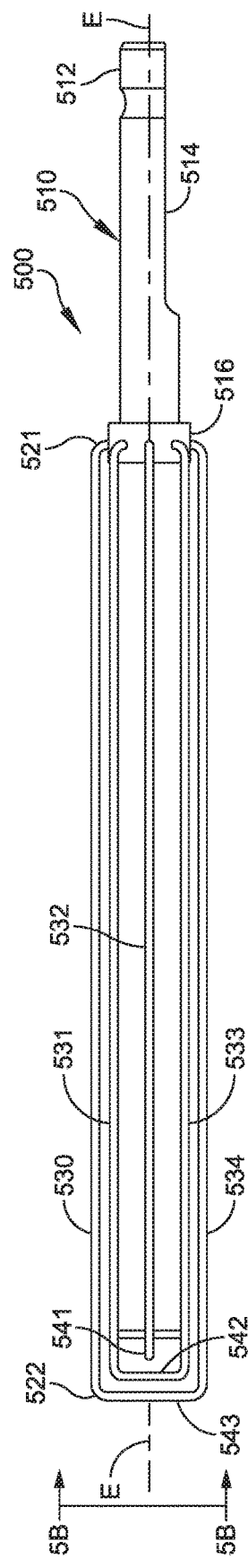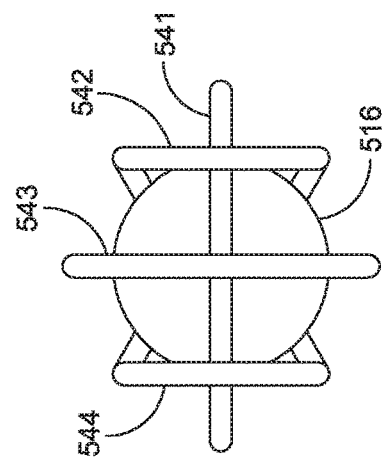
FIG. 4
FIG. 5A
FIG. 5B

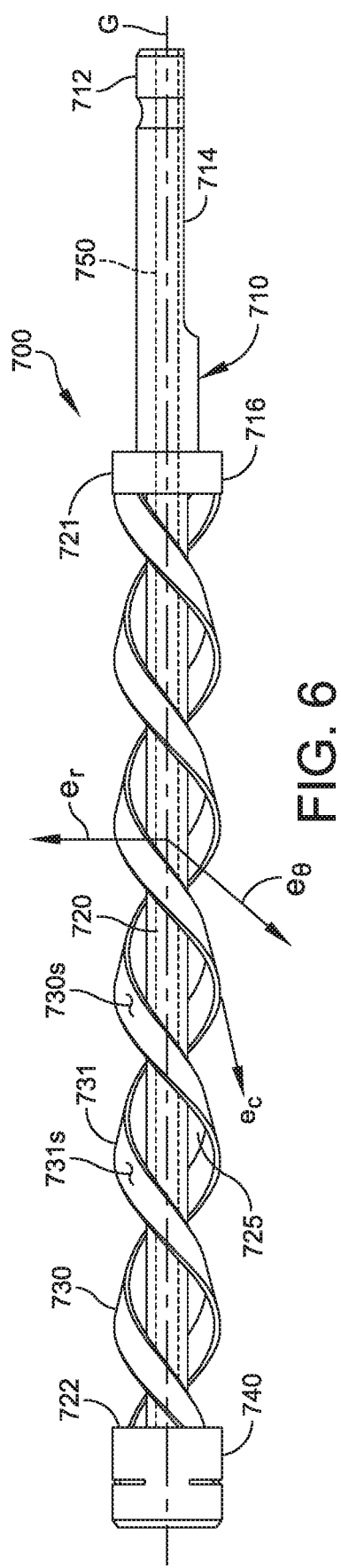
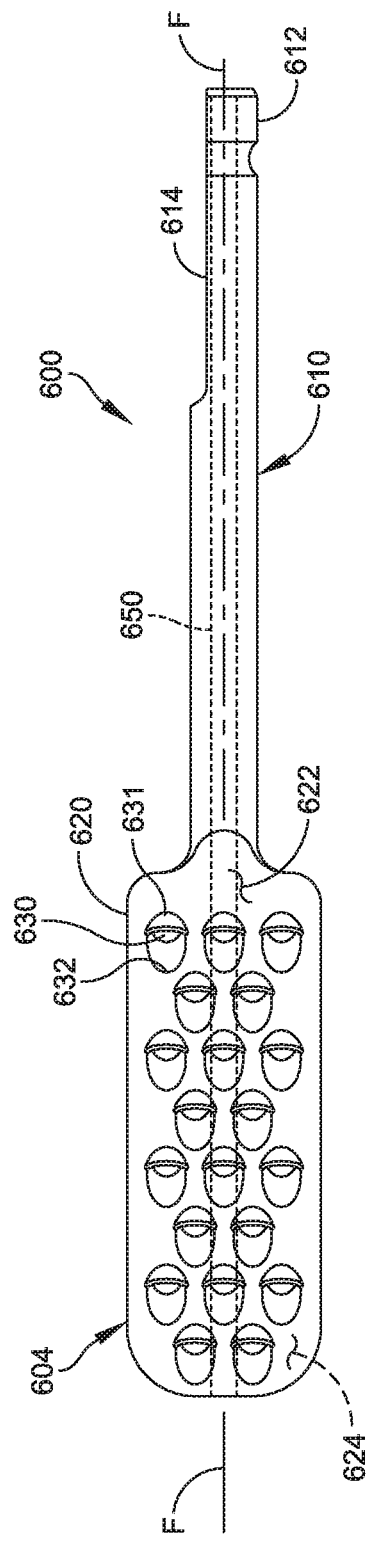
FIG. 6
FIG. 7

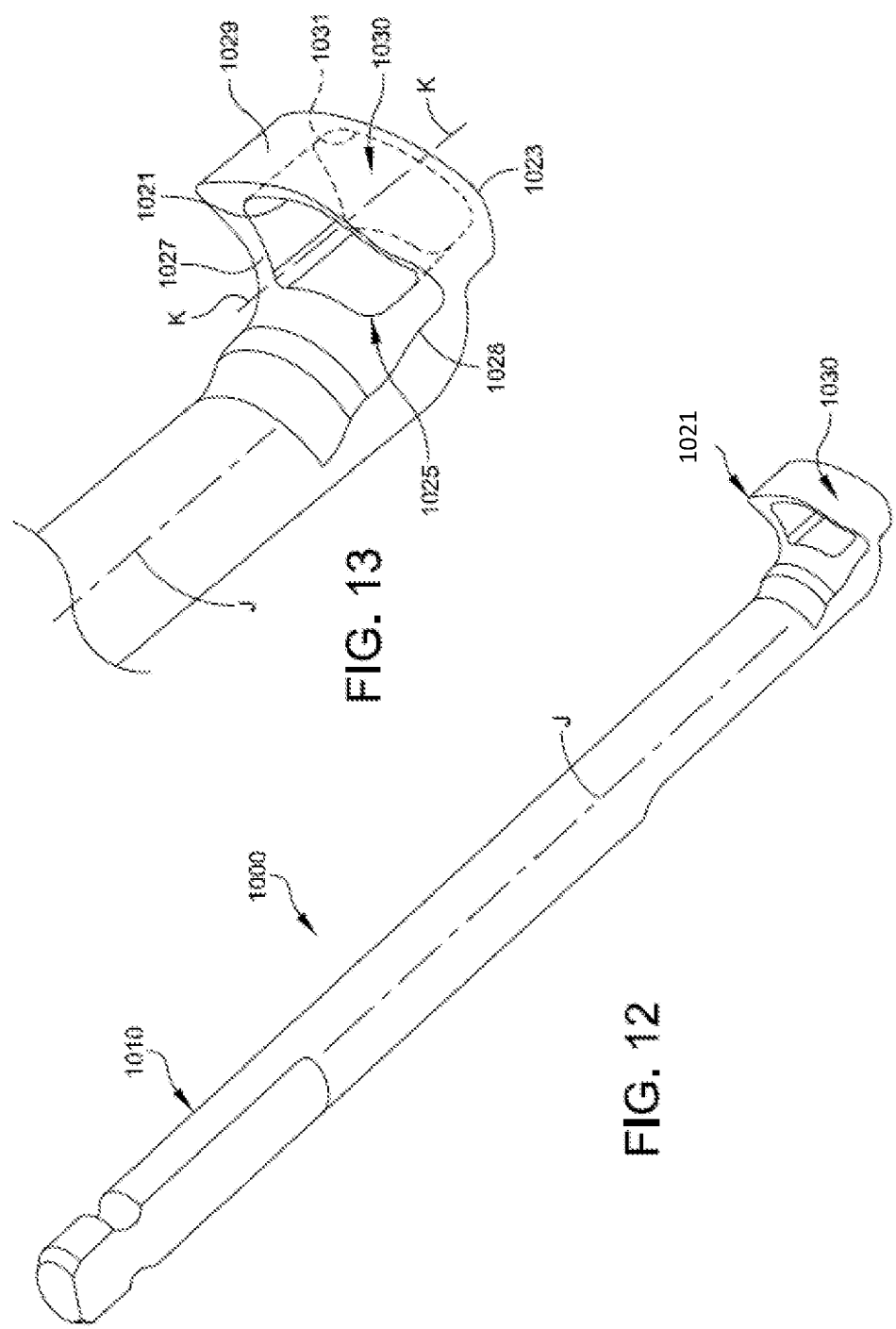

CARTILAGE REMOVAL TOOL AND METHOD

FIELD

This disclosure pertains generally to medical devices, and particularly to surgical tools for cutting and shaping tissue.

BACKGROUND

In a bone fusion procedure, a surgeon removes cartilage from a joint between two adjacent bones and then attaches an implant to both of the two adjacent bones. Proper cartilage removal allows subsequent bone growth between the two adjacent bones to take place. Cartilage removal may be one of the most time-consuming and painstaking steps of a fusion procedure. Cartilage removal has been performed using curettes, rongeurs, or a shaver in an arthroscopic system.

SUMMARY

In some embodiments, an instrument for use in cartilage removal comprises an elongate body having a first end and a longitudinal axis having a longitudinal direction. A cartilage removal portion is coupled to the elongate body at the first end. The cartilage removal portion includes a plurality of serrated blades substantially perpendicular to the longitudinal axis and adapted for removing material while moving in the longitudinal direction. Each serrated blade has a centroid thereof located along the longitudinal axis.

In some embodiments, a method for cartilage removal comprises contacting a cartilage of a patient with a cartilage removal portion of a tool. The cartilage removal portion has a first end, a second end, and a longitudinal axis extending therebetween. The cartilage removal portion includes one or more elongate members disposed radially outward from the longitudinal axis. The one or more elongate members extend parallel to the longitudinal axis from the first end to the second end. The elongate body rotates around the longitudinal axis or reciprocate, so that the one or more elongate extensions cut or abrade the cartilage.

In some embodiments, a method for cartilage removal comprises contacting a cartilage of a patient with a grater. The grater has a shank attached to a plate. The plate has a first face and a second face opposite the first face. The plate defines one or more holes extending therethrough from the first face to the second face. Each hole is defined by a respective cutting edge of the plate. The plate reciprocates, so that the respective cutting edge defines one or more of the holes cuts or abrades the cartilage.

In some embodiments, a method for cartilage removal comprises contacting a cartilage of a patient with a cartilage removal tool having a central longitudinal axis, and at least one rotatable helical strip arranged around the longitudinal axis. The helical strip is separated radially from the longitudinal axis by a space. The at least one helical strip is rotated so that the at least one helical strip revolves around the longitudinal axis and cuts or abrades the cartilage.

In some embodiments, a cartilage removal tool comprises a handle having a longitudinal axis and a distal end. A cartilage removal portion is at the distal end of the handle. The cartilage removal portion has a curved plate with a plurality of serrated blades thereon. Each serrated blade is substantially perpendicular to a major surface of the curved plate. Each serrated blade has a plurality of teeth substantially perpendicular to the major surface. Each serrated blade is adapted for removing material.

In some embodiments, a method of removing cartilage comprises contacting a cartilage with a tool comprising a handle having a longitudinal axis and a trapezoidal tube at an end of the handle. The trapezoidal tube has inner walls defining an opening therethrough. The opening has an axis substantially parallel to the longitudinal axis of the handle. The trapezoidal tube has at least one cutting edge. The tool is moved, so as to cut or grind the cartilage.

BRIEF DESCRIPTION OF THE DRAWINGS

FIG. 4 is a front view of a cartilage removal instrument having four elongated members for cartilage removal.

FIG. 5A is a front view of a cartilage removal instrument having eight elongated members for cartilage removal.

FIG. 5B is an end view of the cartilage removal instrument of FIG. 5A.

FIG. 6 is a side view of a cartilage removal instrument having a pair of helical cutting strips.

FIG. 7 is a top view of a cartilage removal instrument having a plurality of grating features.

FIGS. 12 and 13 show an embodiment of a tool having a trapezoidal tube with a cutting edge.

DETAILED DESCRIPTION

Figure 1A:
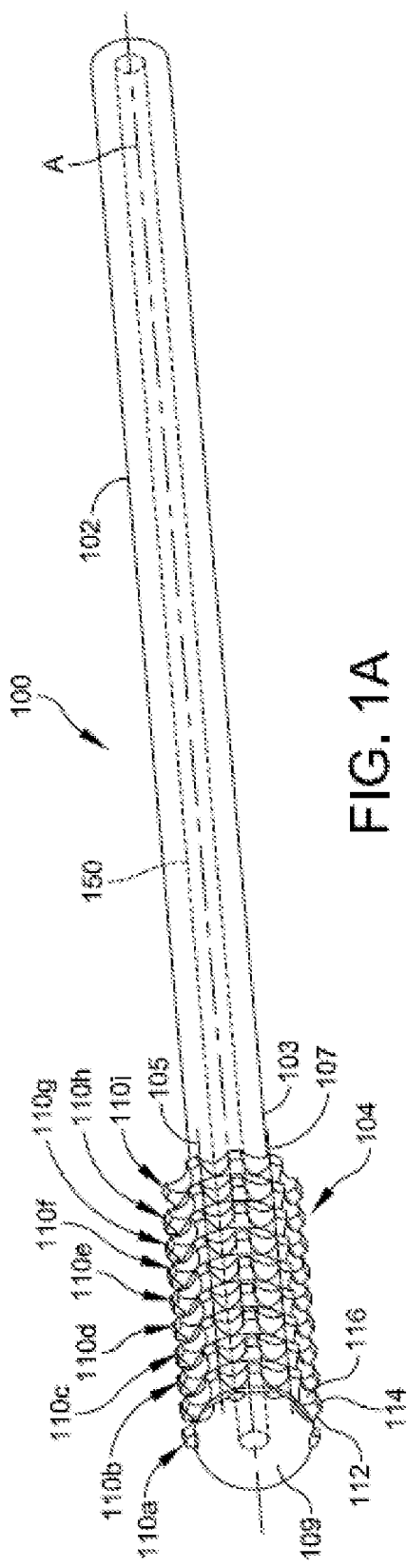
FIG. 1A is an isometric view of an embodiment of a cartilage removal instrument.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, couplings and the like, such as "connected" and "interconnected," refer to a relationship wherein structures are secured or attached to one another either directly or indirectly through intervening structures, as well as both movable or rigid attachments or relationships, unless expressly described otherwise.

This disclosure provides embodiments of a cartilage removal tool suitable for minimally invasive surgery. Various embodiments can be operated by hand, or by attaching the cartilage removal tool to a powered driver instrument for reciprocal or rotational motion.

Any of the embodiments described below can comprise stainless steel or titanium, for example.

Figure 1C:
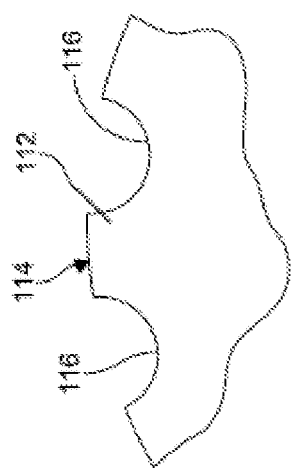
FIG. 1C is an enlarged detail of one of the teeth of FIG. 1A.
Figure 1B:
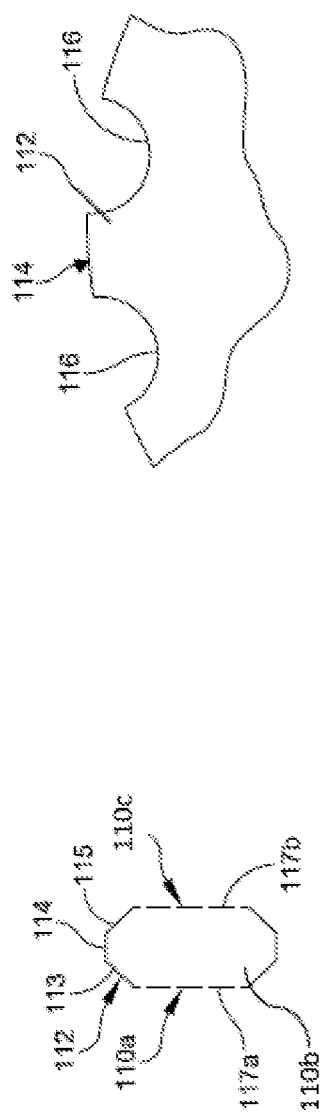
FIG. 1B is a side cross sectional view of one of the blades of the cartilage removal instrument of FIG. 1A.

FIGS. 1A-1C show an instrument 100 for use in cartilage removal. FIG. 1A is an isometric view of the instrument 100. The instrument 100 comprises an elongate body 102 having a first end 103 and a straight longitudinal axis A. The instrument 100 has a cartilage removal portion 104 coupled to the elongate body 102 at the first end 103. The cartilage removal portion 104 includes a plurality of serrated circular blades 110a-110i. Although FIG. 1A shows nine blades 110a-110i, other embodiments can have any number of blades. Each serrated circular blade 110a-110i has a centroid thereof located along the straight longitudinal axis A.

Each of the serrated circular blades 110a-110i has a plurality of teeth 112 arranged around a respective circumference of the blade. The serrated circular blades 110a-110i are substantially perpendicular (i.e., at an angle from 60 degrees to 120 degrees) to the longitudinal axis and adapted for removing material while moving in the longitudinal direction of the longitudinal axis. FIG. 1B is a cross-sectional view of one of the circular blades 100b. FIG. 1C is a front view of one of the circular blades 110a showing the teeth 112. In some embodiments, each of the serrated circular blades 110a-110i has a same number of teeth 112. In FIG. 1A, the serrated circular blades 110a-110i are aligned so that each tooth 112 of a first one of the serrated circular blades 110a lies along a respective straight line segment (e.g., 105 and 107) parallel to the straight longitudinal axis A. Each respective straight line segment 105, 107 passes through a respective tooth 112 of a second one of the serrated circular blades 110b. The instrument 100 is rotationally symmetric about the straight longitudinal axis A. In other embodiments, such as the embodiment shown in FIG. 1D, a given circular blade may be rotationally offset from an adjacent circular blade on one or both sides thereof.

In some embodiments, each of the teeth 112 has a first face 117a and a second face 117b, with a respective bevel 113, 115 on an edge of at least one of the first or second faces 117a, 117b. In some embodiments, as shown in FIG. 1B, each of the teeth 112 has a first face and a second face, with a respective bevel 113, 115 on respective edges of both the first and second faces 117a, 117b. In some embodiments, each of the plurality of teeth 112 has a substantially flat tip 114 at the outer radial edge of the tooth 112. As shown in FIG. 1C, each serrated circular blade 110a-110i, can include a curved concavity 116 between each pair of adjacent teeth 112. In other embodiments (not shown), each concavity can have two flat, planar edges.

Figure 1D:
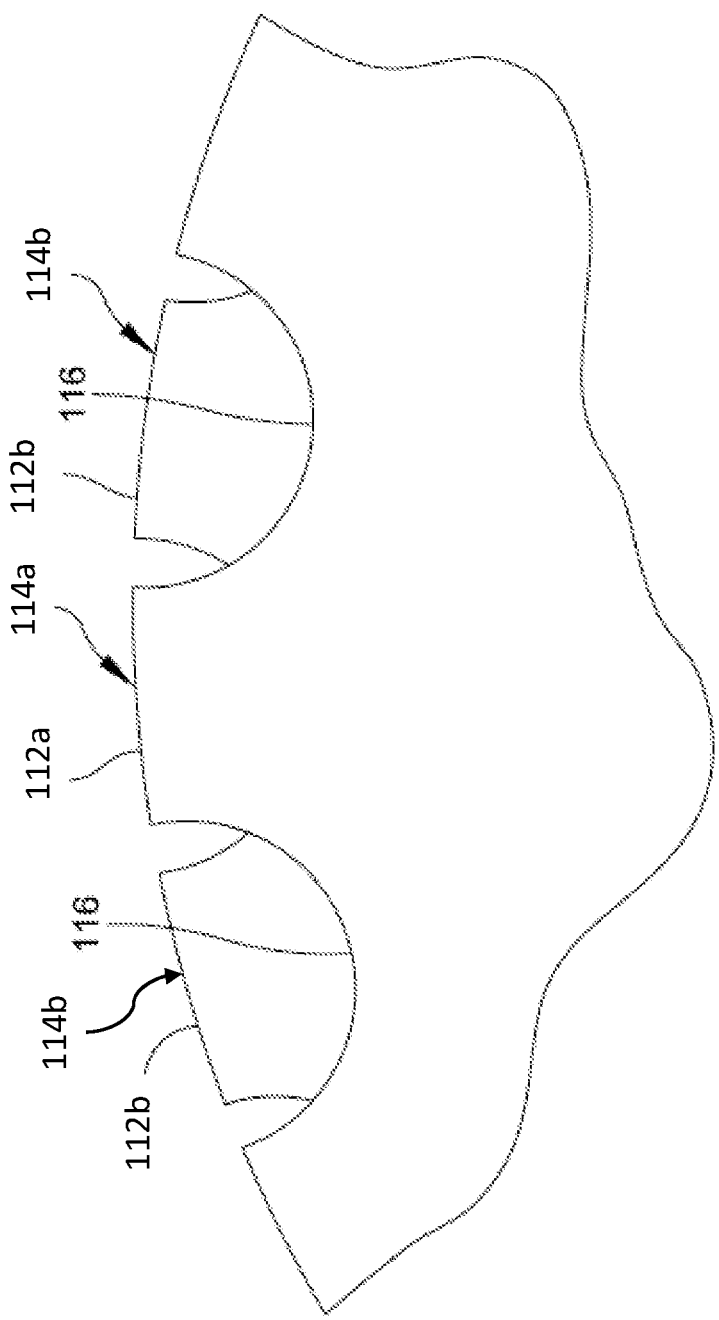
FIG. 1D shows a variation of the arrangement of FIG. 1C, in which the teeth are staggered between adjacent blades.

FIG. 1D shows a variation of the embodiment of FIG. 1C, in which the serrated circular blades 110a-110i are rotationally staggered, so that the teeth 112 of one serrated circular blade 122 are aligned with the curved concavity 116 of the adjacent serrated circular blade. FIG. 1D shows the teeth of two serrated circular blades 110a and 110b in such staggered arrangement. For better identification purposes, the teeth and the flat tips of the first serrated circular blade 110a are identified with reference numbers 112a and 114a whereas the teeth and the flat tips of the second serrated circular blade 110b are identified with reference numbers 112b and 114b. Having the cutting teeth 112 of each of the serrated circular blades 110a-110i be staggered with respect to the teeth 112 on their adjacent serrated circular blades may help with removing cartilage on asymmetric joints.

In some embodiments, as shown in FIG. 1A, the distal end 109 of the instrument 100 has a curved shape, such as a portion of a spheroid, ellipsoid, or paraboloid. The curved distal end helps avoid damage to tissue which the distal end 109 contacts.

FIG. 1B is a cross-sectional view of the serrated circular blade 110b and shows two dashed lines, one dashed line at the boundary between the serrated circular blade 110b and the first adjacent circular blade 110a and a second dashed line at the boundary between the serrated circular blade 110b and the second adjacent serrated circular blade 110c. In some embodiments, the instrument 100 is formed of a single piece of material (e.g., by an additive manufacturing process or sintering or turning/milling), and the dashed lines 117a, 117b correspond to an imaginary boundary between two portions 110a, 110b of the same unitary instrument 100. In other embodiments, each of the serrated circular blades 110a-110i is formed separately, and has faces 117a, 117b. The individual blades 110a-110i are joined together by, for example, adhesive, soldering, or by running a fastener (e.g., a threaded end of the elongated member 102) through a threaded center bore (not shown) in each serrated circular blade 110a-110i.

In some embodiments, the method of using the instrument 100 includes making a small incision over the metatarsophalangeal (MTP) joint (the joint between the metatarsal bones of the foot and the proximal bones, phalanges, of the toes). The surgeon uses a distractor to expand the joint space to allow enough room for the cartilage removal instrument 100 to be placed in the joint space (between metatarsal head and phalanx head). The surgeon inserts the instrument 100 through a cannula into an incision in a patient's skin, and inserting the cartilage removal portion 104 into the vicinity of a joint, so one or more of the teeth 112 contact the cartilage. The instrument 100 can be moved with a reciprocating motion while contacting the cartilage, to cut or grind the cartilage. The instrument 100 can be moved with a reciprocating motion and rotating motion simultaneously while contacting the cartilage, to cut or grind the cartilage. The instrument 100 can be manipulated manually, or the instrument can be driven by a reciprocating tool (such as a reciprocating saw). The surgeon then begins compressing the joint using a distractor, and continues with the procedure/fusion.

In some embodiments, the instrument 100 has a cannula 150, as shown in FIG. 1A. The user can couple the cannula 150 with an irrigation source (not shown), a light source (not shown), and/or an optical sensor coupled to a transmission medium (e.g., optical fiber or cable), allowing the surgeon to ensure that all cartilage has been removed and flushed from the joint space. In other embodiments (not shown), the cannula 150 can be omitted.

Although FIG. 1A shows an instrument 100 with a cylindrical elongated member 102, a drill shank can be substituted for part or all of the elongated member 102, so the instrument is adapted for use with any drill chuck or reciprocating tool chuck.

In FIG. 1A, the blades 110a-110i all have the same size as each other, giving the cartilage removal portion 104 of instrument 100 an approximately cylindrical configuration. In other embodiments (not shown), the cartilage removal portion 104 may have other shapes, such as an egg-shaped or hourglass-shaped portion, to better conform to joint surfaces. That is, the serrated circular blades can have varying sizes to fit within an egg-shaped envelope or an hourglass-shaped envelope.

FIGS. 2-5 show embodiments of a cartilage removal instrument 200, 300, 400, 500 configured for use with a rotating motion.

Figure 2:
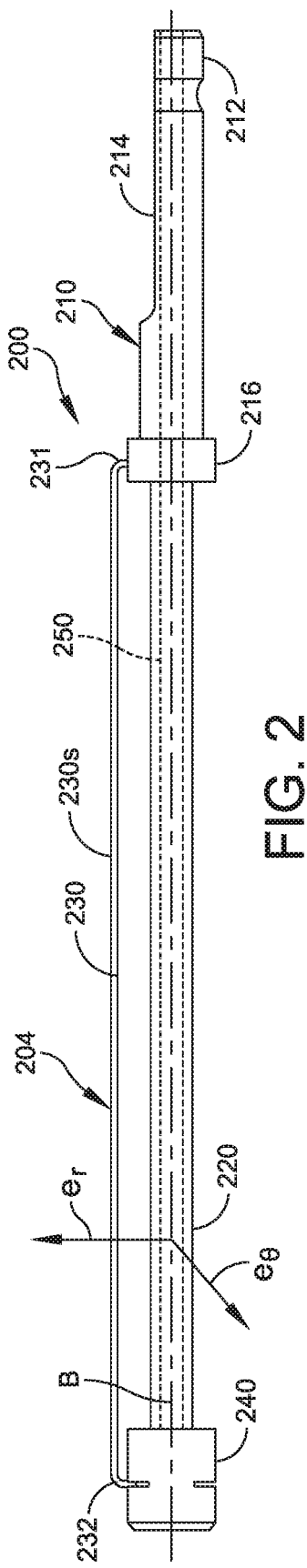
FIG. 2 is a front view of a cartilage removal instrument having an elongated member for cartilage removal.

FIG. 2 shows a cartilage removal instrument 200 having a shank 210 and a cartilage removal portion 204. In some embodiments, the shank 210 is a drill shank having a flat surface 214. In some embodiments, the shank 210 has a quick release connector 212 (e.g., an AO style quick connect shaft) adapted to be received by a tool (not shown) with a corresponding quick-release socket (not shown).

The cartilage removal portion 204 has a first hub 216 at a first end 231 of the cartilage removal portion 204 and a second hub 240 at a second end 232 of the cartilage removal portion 204. A central member 220 extends from the first hub 216 to the second hub 240. The first hub 216 and the second hub 240 are fixed to the elongated member 220 for rotation together about a longitudinal axis B. In the embodiment of FIG. 2, the shank 210, the first hub 216, the second hub 240 and the central member 220 all share the same longitudinal axis B.

The cartilage removal portion 204 includes one or more elongate members 230 disposed radially outward from the longitudinal axis B. The one or more elongate members 230 extend parallel to the longitudinal axis B from the first end 231 to the second end 232. In some embodiments the elongated member 230 has a circular cross-section. In other embodiments, the elongated member 230 has a flat rectangular cross section, with the shorter dimension of the rectangular cross section oriented in the radial direction $e_r$ of the instrument 200 (and the longer dimension of the rectangle in the tangential direction $e_\Theta$). In some embodiments, the elongated member 230 has a flat cross section with at least one sharpened edge oriented in the tangential direction $e_\Theta$, to enhance slicing action when the instrument 200 rotates about the axis B. In some embodiments, the circumferential surface 230s of elongated member 230 (having a surface normal in the radial direction $e_r$) is rough or textured for removing cartilage by shearing. For example, the surface 230s can have a rough diamond coating.

The instrument 200 in FIG. 2 has a shank 210 with a flat or keyed surface 214 and has a mount 212 adapted to be gripped by a quick connect socket of a motorized tool (not shown). In other embodiments, a variety of shafts or shanks can be substituted for the shank 210.

In some embodiments, the method of using the instrument 100 includes making a small incision over the MTP joint. The surgeon uses a distractor to expand the joint space to allow enough room for the cartilage removal instrument 200 to be placed in the joint space (between metatarsal head and phalanx head). The surgeon inserts the instrument 200 through a cannula into an incision in a patient's skin, and inserts the cartilage removal portion 204 into the vicinity of a joint. The shank 210 is rotated, for example, manually or by using a surgical drill having a socket to which the shank 210 is connected. The drill causes the central member 220 and elongate member 230 to rotate around the longitudinal axis B, so that the one or more elongate member 230 cut or abrade the cartilage. The surgeon then begins compressing the joint using a distractor, and continues with the procedure/fusion.

In some embodiments, the instrument 200 has a cannula 250, as shown in FIG. 2. The user can couple the cannula 250 with an irrigation source (not shown), a light source (not shown), and/or an optical sensor coupled to a transmission medium (e.g., optical fiber or cable), allowing the surgeon to ensure that all cartilage has been removed and flushed from the joint space. In other embodiments (not shown), the cannula 250 can be omitted.

In some embodiments, the outer circumferential surface 230s of the elongated member is rough or textured, and cartilage can be abraded or ground by rotating or reciprocating the instrument 200.

Figure 3:
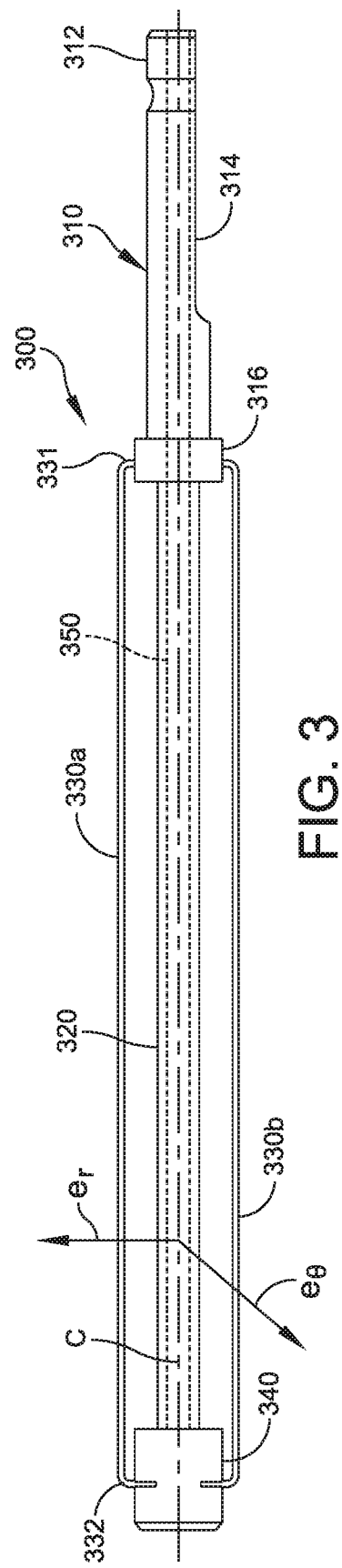
FIG. 3 is a front view of a cartilage removal instrument having two elongated members for cartilage removal.

FIG. 3 shows a cartilage removal instrument 300, which is a variation of the instrument 200 of FIG. 2. The shank 310, quick connect 312, flat surface 314, first hub 316, central member 320, first end 331, second end 332 and second hub 340 can be the same as the shank 210, quick connect 212, flat surface 214, first hub 216, central member 220, first end 231, second end 232, and second hub 240, respectively, described above. For brevity, descriptions of these common elements are not repeated. The method of using the cartilage removal instrument 300 can also be the same as the method of using the cartilage removal instrument 200 described above, and, solely for brevity, the description of use is not repeated.

In some embodiments, the cartilage removal instrument 300 has two elongated members 330a, 330b. In some embodiments, the elongated members are spaced 180° apart, on opposite sides of the central member 320, to better balance the distribution of mass of the elongated members 330a, 330b around the longitudinal axis C. When the instrument 300 is rotated, the balanced mass may reduce or prevent wobble and/or vibration, for smoother cartilage removal.

In some embodiments, the instrument 300 has a cannula 350, as shown in FIG. 3, which can be used as discussed above with respect to cannula 150 in FIG. 1A. In other embodiments (not shown), the cannula 350 can be omitted.

FIG. 4 shows a cartilage removal instrument 400, which is a variation of the instrument 200 of FIG. 2. The shank 410, quick connect 412, flat surface 414, first hub 416, first end 421, can be the same as the shank 210, quick connect 212, flat surface 214, first hub 216, first end 231, respectively, described above. For brevity, descriptions of these common elements are not repeated. The method of using the cartilage removal instrument 400 can also be the same as the method of using the cartilage removal instrument 200 described above, and, solely for brevity, the description of use is not repeated.

In some embodiments, the cartilage removal instrument 400 has four elongated members 430, 431, 432, and a fourth elongated member (not shown) evenly spaced 90° apart, to better balance the distribution of mass of the elongated members 430, 431, 432, . . . around the longitudinal axis D. (The fourth member is positioned spaced 180° apart from elongated member 431.) When the instrument 400 is rotated, the balanced mass may reduce or prevent wobble and/or vibration, for smoother cartilage removal.

The cartilage removal instrument 400 can omit a second hub at the second end 422. In some embodiments, each elongated member (e.g., 430, 432) has a respective radial portion (e.g., 430e, 432e) extending from the central longitudinal axis D to the end of the respective elongated member 430, 432, . . . . The radial portions 430e, 432e, . . . can be attached to each other (e.g., by welding or soldering) at their intersection along the longitudinal axis D. In other embodiments (not shown), an instrument has a second hub at the second end 422, to which the four elongated members 430, 431, . . . are attached. In some embodiments, the outer end surface of the radial portions 430e, 432e, . . . can be rough or textured, and can be held against cartilage while rotating the shank or shaft 410, to remove material.

FIGS. 5A-5B show a cartilage removal instrument 500, which is a variation of the instrument 400 of FIG. 4. FIG. 5A is a side view of the cartilage removal instrument 500, and FIG. 5B is front view. The shank 510, quick connect 512, flat surface 514, and first hub 516, and first end 521 can be the same as the shank 410, quick connect 412, flat surface 414, first hub 416, and first end 421, respectively, described above. For brevity, descriptions of these common elements are not repeated. The method of using the cartilage removal instrument 500 can also be the same as the method of using the cartilage removal instrument 200 described above, and, solely for brevity, the description of use is not repeated.

In some embodiments, the cartilage removal instrument 500 has eight elongated members 530, 531, 532, . . . evenly spaced 45° apart, to better balance the distribution of mass of the elongated members 530, 531, 532, . . . around the longitudinal axis E. When the instrument 500 is rotated, the balanced mass may reduce or prevent wobble and/or vibration, for smoother cartilage removal. In other embodiments, the eight elongated members 530, 531, 532, . . . may all be included in a single continuous wire having a plurality of bends (not shown), embedded within the first hub 516.

The cartilage removal instrument 500 can omit a second hub at the second end 522. In some embodiments, the elongated members (e.g., 530, 532 . . . ) are arranged in pairs, and the elongated members within each pair are connected to each other by a perpendicular member at the second end 522 of the instrument 500. FIG. 5B shows an arrangement in which, proceeding counterclockwise from a first elongated member at the 3 o'clock position, the pairs include the first and fifth elongated members (connected by member 541), the second and eighth elongated members (connected by member 542), the third and seventh elongated members (connected by member 543), and the fourth and sixth elongated members (connected by member 544). The end portions 541, 542, . . . can be attached to their respective elongated members (e.g., by welding or soldering) at the second end 522 of the cartilage removal instrument 500. Alternatively, the end portions 541, 542, . . . can be formed from the same wire as their respective elongated members. In other embodiments (not shown the instrument has a second hub at the second end 522, to which the eight elongated members 530, 531, . . . are attached.

The cartilage removal instruments 200, 300, 400 and 500 can shave off cartilage while not damaging bone in the region.

FIG. 6 shows a cartilage removal instrument 700, which is a variation of the instrument 200 of FIG. 2. The shank 710, quick connect 712, flat surface 714, first hub 716, central member 720, first end 721, second end 722 and second hub 740 can be the same as the shank 210, quick connect 212, flat surface 214, first hub 216, central member 220, first end 231, second end 232, and second hub 240, respectively, described above. For brevity, descriptions of these common elements are not repeated. The method of using the cartilage removal instrument 700 can also be the same as the method of using the cartilage removal instrument 200 described above, and, solely for brevity, the description of use is not repeated.

In some embodiments, the cartilage removal instrument 700 has two elongated helical strips 730, 731 separated radially from the longitudinal axis G by an annular space 725. Because of the annular space 725, the helical strips 730, 731 have continuous helical cutting edges facing in a direction $e_c$ orthogonal to the radial direction). In some embodiments, the elongated strips 730, 731 are phased 180° apart, on opposite sides of the central member 720, to better balance the distribution of mass of the helical strips 730, 731 around the longitudinal axis G; the annular space 725 is located radially between the central member 720 and the helical strips 730, 731. When the instrument 700 is rotated, the leading edge of each helical strips 730, 731 contacts and cuts or abrades the cartilage.

In some embodiments, each elongated helical strips 730, 731 has a flat rectangular cross section, with the shorter dimension of the rectangular cross section oriented in the radial direction $e_r$ of the instrument 200 (and the longer dimension of the rectangle in the tangential direction $e_\Theta$). In some embodiments, the elongated helical strips 730, 731 have a flat cross section with at least one sharpened edge oriented in the tangential direction $e_\Theta$, to enhance slicing action when the instrument 700 rotates about the axis G. In some embodiments, the circumferential surface 730s, 731s of elongated helical strips 730, 731 (having a surface normal in the radial direction $e_r$) is rough or textured for removing cartilage by shearing.

The helical strips 730, 731 can be used to shave off the cartilage. The angled cutting edge of each helical strip aids in directing cartilage away from the site once the cartilage has been removed, to prevent clogging of the instrument 700. The helical strips 730, 731 may be dull or curved inward (to only remove cartilage), or sharp (to aid in slight removal of bone to expose an appropriate amount of healthy, bleeding bone to aid in fusion).

In some embodiments, the instrument 700 has a cannula 750, as shown in FIG. 6, which can be used as discussed above with respect to cannula 150 in FIG. 1A. In other embodiments (not shown), the cannula 750 can be omitted.

FIG. 7 is a side view of an embodiment of a cartilage removal device in the form of a grater 600 suitable for a grating or abrasion action. The grater 600 has a shank 610 and a cartilage removal portion 604 attached to the shank 610. The cartilage removal portion 604 includes a plate 620 having a first face 622 and a second face 624 opposite the first face 622.

The plate 620 defines one or more holes 630 extending through the plate 620 from the first face 622 to the second face 624. The rows of holes 630 can be arranged staggered, as shown in FIG. 7, so that each row is offset from the preceding and/or succeeding row by half the pitch between adjacent holes within a row. In other embodiments (not shown), the rows and columns of holes 630 are aligned in a rectangular grid, without any offset between adjacent holes within the same column.

Each hole 630 is defined by a respective cutting edge of the plate. In some embodiments, the plate 620 has a respective scallop-shaped scoop 631 adjacent each respective hole 630 in the array of holes. When the plate moves or reciprocates in the direction of longitudinal axis F, the scallop-shaped scoops 631 and the edges surrounding the holes 630 cut or abrade the cartilage, and the scallop-shaped scoops deflect the cut or abraded cartilage into their respective holes. The scallop-shaped scoops 631 may be dull (to only remove cartilage), or sharp (to aid in removal of a small amount of bone, to expose an appropriate amount of healthy, bleeding bone to aid in fusion).

In some embodiments, the plate includes a concave indentation 632 adjacent each hole 630, so that the hole 630 is between a respective indentation 632 and scallop-shaped scoop 631. The indentation 632 allows the cartilage to extend below the surface 622 of the plate 620 (i.e., into the page of FIG. 7), so the hole 630 and scallop-shaped scoop 631 slice or abrade more deeply into the cartilage.

In operation, the instrument 600 is used by inserting the instrument 600 through a cannula (not shown) into an incision in the patient's skin, and inserting the cartilage removal portion 604 into the vicinity of a joint. The instrument 600 is positioned so the cartilage removal portion 604 contacts the cartilage of the patient. The shank 610 is reciprocated, for example using a reciprocating tool having a socket to which the quick connect 612 and flat surface 614 of shank 610 is connected. The reciprocating tool causes the cartilage removal portion 604 to move back and forth in a direction parallel to the longitudinal axis F, so that the cutting edges defining one or more holes 630 and the respective scallop-shaped scoops 631 slice or abrade the cartilage. In other embodiments of the method, the surgeon can manually reciprocate the instrument 600 without using a motorized tool.

In some embodiments, the instrument 600 has a cannula 650, as shown in FIG. 7, which can be used as discussed above with respect to cannula 150 in FIG. 1A. In other embodiments (not shown), the cannula 650 can be omitted.

Figures 8, 9:
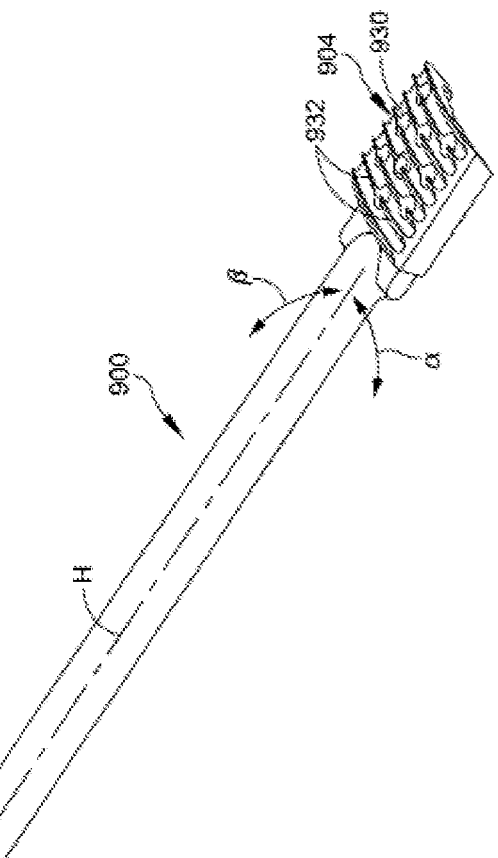
FIG. 8 is an isometric view of another cartilage removal instrument having a plurality of grating features.
FIG. 9 is an enlarged detail of the grater of FIG. 8.
Figure 10:
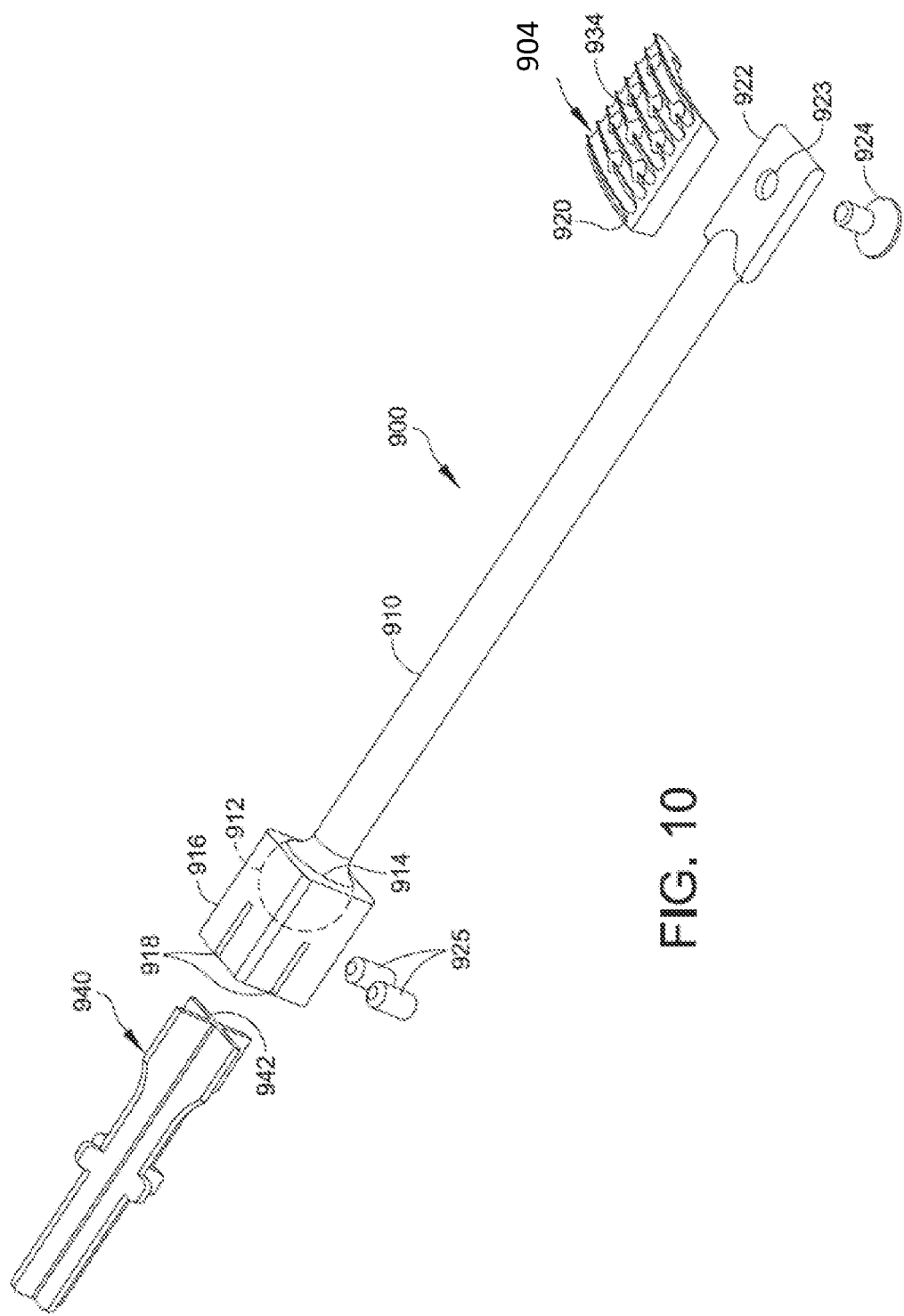
FIG. 10 is an exploded view of the cartilage removal instrument of FIG. 8.

FIGS. 8-10 show an instrument 900, which is a variation of the instrument 600 of FIG. 7. FIG. 8 is an isometric drawing of the instrument 900. FIG. 9 is an enlarged detail of the cartilage removal portion 904 of FIG. 8. FIG. 10 is an exploded view of the instrument 900. The instrument 900 has a shank 910 and a grater 904. The grater 904 is attached to the shank 910. The grater 904 has a plate 920 having a first face 920a and a second face 920b opposite the first face 920a. The plate 920 defines one or more holes 930 extending therethrough from the first face 920a to the second face 920b. Each hole 930 is defined by a respective cutting edge of the plate 920 surrounding the hole 930.

The plate 920 includes at least a first blade 932 and a second blade 934. The first and second blades 932, 934 are substantially perpendicular (i.e., at an angle from 60 degrees to 120 degrees) to a longitudinal axis H of the shank 910 and adapted for removing material while moving in the longitudinal direction of the longitudinal axis. At least one of the one or more holes 930 are located at a center of the first blade 932, separating the first blade 932 into two blade portions. The second blade 934 is parallel to the first blade 932 and adjacent to the at least one hole 930. The second blade 934 is configured to deflect cartilage into the at least one hole 930 during the reciprocating motion. For example, as shown in FIG. 9, the second blade 934 is sloped toward the hole 930. When the instrument 900 contacts cartilage and is moved in the direction of axis H so that the hole 930 reaches a given point on the cartilage before the blade 934 reaches that same point, blade 934 scrapes cartilage and deflects the cartilage toward the hole 930. In the same way, each of the holes 930 is adjacent a respective blade that can deflect cartilage toward that respective hole 930.

The method of using the instrument 900 includes contacting a cartilage of a patient with the grater 904. The grater 904 has a shank 910 attached to a plate 920. The plate 920 has a first face 920a and a second face 920b opposite the first face 920a. The plate 920 defines one or more holes 930 extending therethrough from the first face 920a to the second face 920b, where each hole 930 is defined by a respective cutting edge of the plate 920. In some embodiments, a reciprocating tool is used to reciprocate the plate 920 so that the respective cutting edge 934 defining one or more of the holes 930 cuts or abrades the cartilage.

The instrument 900 includes a type of shank 910 that can be connected to a reciprocating tool. The shank 910 of the instrument 900 has a ball 912 extending part way through a circular opening 914 in a housing 916. The attachment portion 940 has a cross-shaped end 942 that is adapted to be received in mating slots 918 of the housing 916. The attachment portion 940 retains the ball 912 within the housing, while allowing angular rotations $\alpha$ and $\beta$ (shown in FIG. 8) of the shank 910 in two orthogonal directions. The ball mount allows the reciprocating tool to be oriented at an angle relative to the longitudinal axis H of the shank 910, to access hard-to-reach joints.

FIG. 10 is an exploded view of the instrument 900. The shank 910 has a mounting plate 922 at the end opposite the attachment portion 940. The plate 920 can be attached to the mounting plate 922 by a screw 924, rivet, or the like inserted through the hole 923 in the mounting plate 922. In some embodiments, the plate 920 is used for one surgical procedure, removed, and replaced with a fresh plate 920. The attachment portion 940 can be secured to the housing 916 by set screws 925 or other fasteners.

Figure 11:
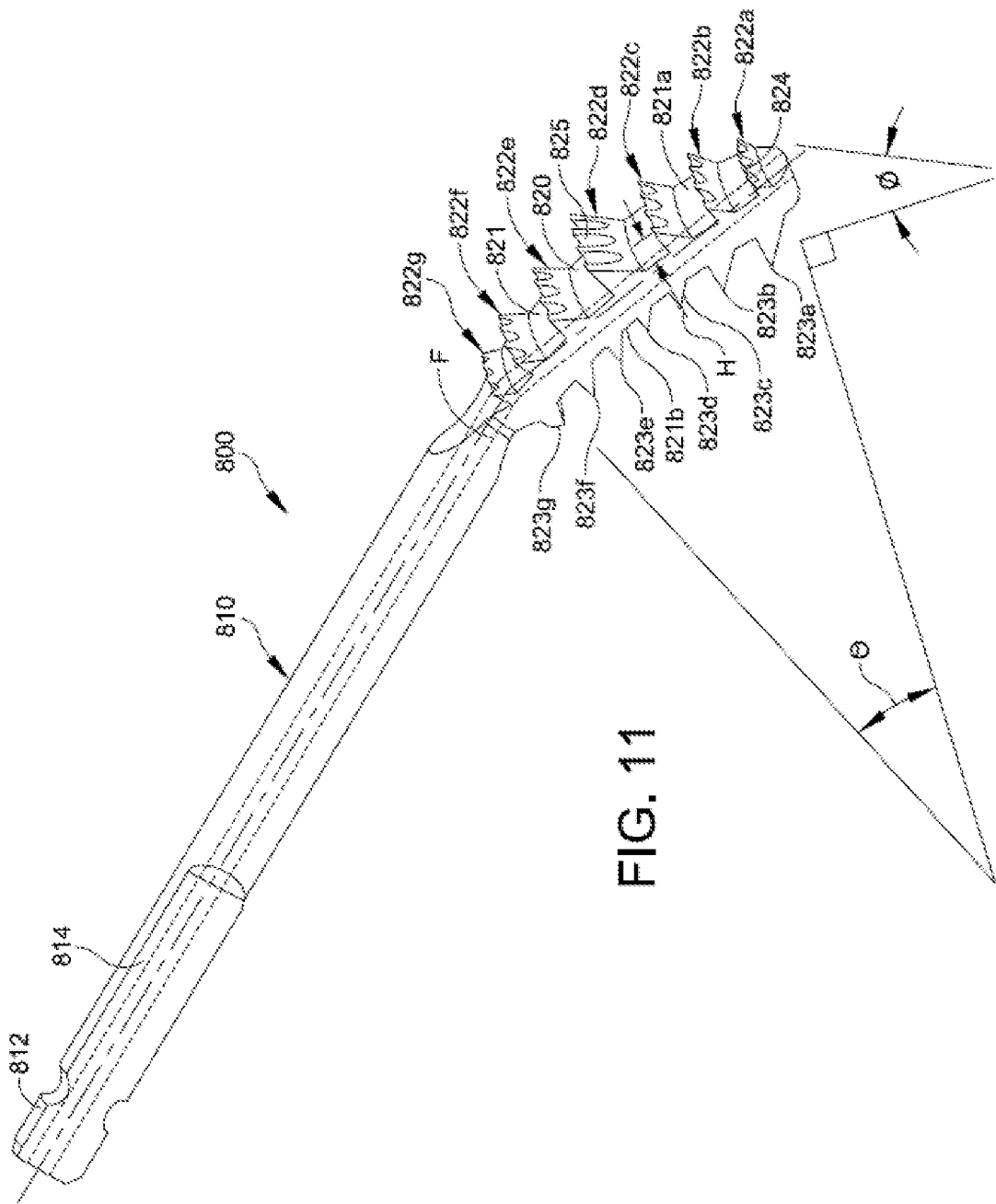
FIG. 11 is an isometric view of a cartilage removal tool having convex and concave sides.

FIG. 11 shows another embodiment of a cartilage removal tool 800. The tool 800 has a handle or shank 810 having a quick connect 812, a flat surface 814, a longitudinal axis F and a distal end. A cartilage removal portion 820 is attached at the distal end of the handle or shank 810. The cartilage removal portion 820 has a curved plate 821. In some embodiments, the plate 821 of the cartilage removal portion 820 has a curvature in two perpendicular directions. The curvature in the first direction is shown by the angle of curvature $\Theta$ in a plane containing the longitudinal axis F. The curvature in the second direction is shown by the angle of curvature $\phi$ in a plane orthogonal to the longitudinal axis F. The curved plate 821 has a convex side 821a and a concave side 821b. In some embodiments, the convex side is convex in the directions of both $\Theta$ and $\phi$, and the concave side 821b is concave in the directions of both $\Theta$ and $\phi$. In other embodiments (not shown), the plate 821 is curved in the plane of the angle $\Theta$, but the angle $\phi$ is zero. In another embodiments (not shown), the plate 821 is curved in the plane of the angle $\phi$, but the angle $\Theta$ is zero.

The curved plate 821 has a plurality of serrated blades 822a-822g, 823a-823g thereon. Each serrated blade 822a-822g, 823a-823g has a plurality of teeth 824. Each tooth 824 has a ramped surface increasing in height H from a distal end of the tooth 824 to a proximal end of the tooth 824. Within each blade 822a-822g, 823a-823g, each pair of adjacent teeth 824 has a concave surface 825 between the pair of adjacent teeth 824.

Each serrated blade 822a-822g, 823a-823g is substantially perpendicular to the longitudinal axis F of the handle or shank 810. For example, in FIG. 11, each blade 822a-822g is substantially perpendicular (e.g., from 60 degrees to 120 degrees) to the convex surface 821a, and each blade 823a-823g is substantially perpendicular to the concave surface 821b. In FIG. 11, since the plate 821 is curved in the plane of the angle $\phi$, and the surface 821a is convex in the plane of the angle $\phi$, each blade 822a-822g has a curvature in the plane of the angle $\phi$. For example, in FIG. 11, the exemplary range of $\Theta$ can be in a range from 0 degrees to 45 degrees, and in some embodiments, can be a range from 10 degrees to 30 degrees, and in some embodiments, in a range from 20 degrees to 30 degrees. Also, in FIG. 11, the exemplary range of $\phi$ can be from 0 degrees to 30 degrees, and in some embodiments, can be a range from 5 degrees to 20 degrees, and in some embodiments, in a range from 10 degrees to 15 degrees. The base and the cutting edge of each blade 822a-822g, 823a-823g are curved in the plane of the angle $\phi$ by the same angle as the corresponding convex and concave surfaces 821a and 821b.

In some embodiments, the serrated blades 822a-822g, 823a-823g have a plurality of different heights. In some embodiments, the height H of the serrated blades 822a-822g on the convex side 821a can have a first height value at or near the proximal end or the distal end of the cartilage removal portion 820 and at least one second height value between the proximal end and the distal end of the cartilage removal portion 820, where the second height is greater than the first height. In some embodiments, the serrated blades 823a-823g on the concave side 821b have a third height value at or near the proximal end or the distal end of the cartilage removal portion and at least one fourth height value between the proximal end and the distal end of the cartilage removal portion, where the fourth height is less than the third height.

For example, in FIG. 11, the heights increase from blade 822a to 822d, and then decrease from blade 822d to 822g; the heights decrease from blade 823a to 823d, and then increase from blade 823d to 823g. Thus, the cutting edges of the blades 822a-822g lie along a convex envelope, which may be an ellipsoid, paraboloid, ovoid or the like. Similarly, the cutting edges of the blades 823a-823g lie along a concave envelope, which may be an ellipsoid, paraboloid, ovoid or the like. The blades on the convex side 821a or the concave side 821b are adapted to remove material when the instrument 800 is moved in the direction of the convex side 821a or the concave side 821b, respectively. In this configuration, the side of the cartilage removal corresponding to the convex side 821a of plate 821 is adapted for removing cartilage from concave surfaces, and the side of the cartilage removal corresponding to the concave side 821b of plate 821 is adapted for removing cartilage from convex surfaces.

In operation, the instrument 800 can be oscillated manually or by attachment to a reciprocating tool. The combination of curved, concave and convex sides can remove cartilage and aid in removal of thin layers of bone to expose an appropriate amount of healthy, bleeding bone to aid in fusion. The curved concave/convex shape of instrument 800 can be used for the cup/cone joint prep for joint fusion.

FIGS. 12 and 13 show a tool 1000 used in another method of removing cartilage. The tool 1000 comprises a handle or shank 1010 having a longitudinal axis J and a substantially isosceles trapezoid shaped tube 1030 at an end of the handle or shank 1010. The trapezoidal tube 1030 has inner walls 1031 defining an opening 1025 therethrough. The opening 1025 has an axis K substantially parallel to the longitudinal axis J of the handle or shank 1010. The trapezoidal tube 1030 has at least one cutting edge 1021, 1023. For example, the tube 1030 can have a proximal cutting edge 1021 and a distal cutting edge 1023. In some embodiments, the lateral sides 1027 and 1028 of the isosceles trapezoid shaped tube 1030 have additional cutting edges. In some embodiments, the outer surface 1029 can be rough or textured for fine abrasion and removal of thin layers of remaining cartilage.

In operation, the surgeon contacts a cartilage with the tool 1000. The surgeon can use the cutting edge 1021 to manually cut the cartilage while withdrawing the tool 1000 from the joint. Alternatively, the surgeon can manually reciprocate the tool 1000, so as to cut the cartilage with both the edges 1021 and 1023. For fine adjustments, the surgeon can contact the cartilage with the outer surface 1029 and manually reciprocate the tool 1000 to remove a thin layer of cartilage.

Although the subject matter has been described in terms of exemplary embodiments, it is not limited thereto. Rather, the appended claims should be construed broadly, to include other variants and embodiments, which may be made by those skilled in the art.

What is claimed is:

1. An instrument for use in cartilage removal, the instrument comprising:
    an elongate body having a first end and a second end and defining a straight longitudinal axis therethrough defining a longitudinal direction; and,
    a cartilage removal portion coupled to the elongate body at the first end, wherein the cartilage removal portion extends straight along the straight longitudinal axis and terminating at a point that defines a distal end of the instrument,
        wherein the cartilage removal portion consisting of a plurality of serrated blades that are all substantially perpendicular to the straight longitudinal axis and adapted for removing material while moving in the longitudinal direction, each serrated blade having a centroid thereof located along the longitudinal axis,
    wherein the distal end of the instrument has a curved shape that is a hemisphere of a spheroid, an ellipsoid, or a paraboloid.

2. The instrument of claim 1, wherein each of the blades has a circular plate with a plurality of teeth arranged around a respective circumference.

3. The instrument of claim 2, wherein:
    the serrated blades are aligned so that each tooth of a first one of the serrated blades lies along a respective straight line segment parallel to the straight longitudinal axis, and
    each respective line segment passes through a respective tooth of a second one of the serrated blades.

4. The instrument of claim 2, wherein each of the serrated circular blades has a same number of teeth.

5. The instrument of claim 2, wherein each of the plurality of teeth has a first face and a second face each facing in an opposite direction along the longitudinal direction, with a respective bevel on an edge of at least one of the first or second faces.

6. The instrument of claim 2, wherein each of the plurality of teeth has a first face and a second face each facing in an opposite direction along the longitudinal direction, with a respective bevel on respective edges of the first and second faces.

7. The instrument of claim 2, wherein each of the plurality of teeth has a substantially flat tip.

* * * * *